United States Patent [19]

Nohara et al.

[11] 4,255,576
[45] Mar. 10, 1981

[54] 1-AZAXANTHONE DERIVATIVES

[75] Inventors: Akira Nohara, Kyoto; Hirosada Sugihara, Osaka; Kiyoshi Ukawa, Toyonaka, all of Japan

[73] Assignee: Takeda Chemical Industries, Ltd., Osaka, Japan

[21] Appl. No.: 970,105

[22] Filed: Dec. 18, 1978

Related U.S. Application Data

[63] Continuation-in-part of Ser. No. 881,237, Feb. 27, 1978, Pat. No. 4,143,042.

[30] Foreign Application Priority Data

| Mar. 8, 1977 [JP] | Japan | 52-25654 |
| Mar. 8, 1977 [JP] | Japan | 52-25655 |
| Dec. 20, 1977 [JP] | Japan | 52-153898 |

[51] Int. Cl.³ .................................. C07D 491/052
[52] U.S. Cl. .................................. 546/92; 546/62; 546/89
[58] Field of Search .................. 546/89, 92, 62

[56] References Cited

U.S. PATENT DOCUMENTS

| 3,803,153 | 4/1974 | Villani | 546/89 |
| 3,931,199 | 1/1976 | Nakanishi et al. | 546/89 |
| 4,066,655 | 1/1978 | Connor et al. | 546/92 |

OTHER PUBLICATIONS

Petersen et al., Liebigs Amm. Chem. 1976, p. 1659-1662.

*Primary Examiner*—Henry R. Jiles
*Assistant Examiner*—Natalie Harkaway
*Attorney, Agent, or Firm*—Wegner & Bretschneider

[57] ABSTRACT

The present invention relates to novel 1-azaxanthone derivatives, which are shown by the following formula:

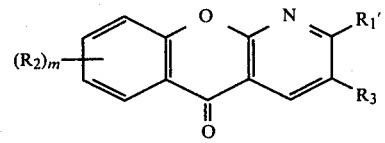

wherein
m is 1 or 2
$R'_1$ is hydrogen, $C_{1-6}$ alkyl, phenyl, $C_{1-6}$ alkoxycarbonyl, hydroxy, $C_{1-4}$ alkoxy, amino or $C_{1-3}$ alkylamino;
each of $R_2$ is independently $C_{1-6}$ alkyl, $C_{1-4}$ alkoxy, halogen, nitro, hydroxy, carboxy, amino, $C_{1-3}$ alkylamino or di($C_{1-3}$ alkyl) amino; or
when m is 2, the two $R_2$ groups may be independently as defined above or may form together with adjacent rings carbon atoms the butadienylene group;
$R_3$ is cyano, $C_{1-6}$ alkoxycarbonyl, carboxamide, N-$C_{1-3}$ alkylcarboxamide or N,N-di($C_{1-3}$alkyl) carboxamide.

The novel derivatives are useful as intermediates for 1-azaxanthone-3-carboxylic acid derivatives having effective antiallergic and bronchodilating activities.

23 Claims, No Drawings

1-AZAXANTHONE DERIVATIVES

This is a continuation-in-part of Ser. No. 881,237, now filed Feb. 27, 1978, now U.S. Pat. No. 4,143,042, granted Mar. 6, 1979.

The present invention relates to novel 1-azaxanthone-3-carboxylic acid and its derivatives which have excellent pharmacological activities. More particularly, the present invention provides novel 1-azaxanthone-3-carboxylic acid and its derivatives of the formula (I)

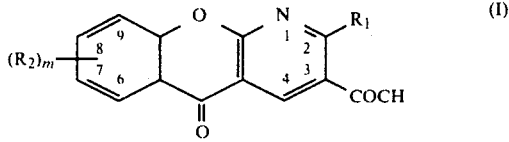

wherein $R_1$ is hydrogen, alkyl, phenyl, carboxyl, hydroxyl, alkoxy or amino group which may be unsubstituted or substituted by one alkyl, m is 0, 1 or 2 and $R_2$ is alkyl, alkoxy, halogen, nitro, hydroxy, carboxyl, butadienylene (—CH=CH—CH=CH—) which forms a benzene ring with any adjacent carbon atoms or amino group which may be unsubstituted or substituted by at least one alkyl, and their physiologically acceptable salts, which have excellent pharmacological activities such as antiallergic and bronchodilating activities.

The object compounds of formula (I) may be produced by hydrolyzing the compounds of the formula (II)

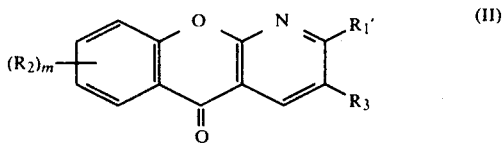

wherein $R'_1$ is hydrogen, alkyl, phenyl, alkoxycarnonyl, hydroxyl, alkoxy, or amino group which may be unsubstituted or substituted by one alkyl, m and $R_2$ have the same meaning as defined above and $R_3$ is cyano, alkoxycarbonyl, carboxamide which may be unsubstituted or substituted by at least one alkyl.

The substituents designated in each of the abovementioned formulae may be substituted at optional position or positions of the 6-, 7-, 8- or 9-positions of the azaxanthone ring.

In the formula (I), the alkyl group represented by $R_1$ and $R_2$ may be any of straight-chain, branched or cyclic alkyl group having 1 to 6 carbon atoms. Typical examples of the alkyl group may be methyl, ethyl, propyl, isopropyl, butyl, isobutyl, sec.-butyl, tert.-butyl, pentyl, cyclopentyl, hexyl, cyclohexyl, etc. Among them, for practical purposes, lower alkyls having 1 to 3 carbon atoms are preferred.

The alkoxy group represented by $R_1$ and $R_2$ may for example be that having 1 to 4 carbon atoms in the alkyl moieties, such as methoxy, ethoxy, propoxy, isopropoxy, butoxy, etc.

The mono-alkyl substituted amino group represented by $R_1$ may be that having 1 to 3 carbon atoms in the alkyl moieties, such as methylamino, ethylamino, propylamino or isopropylamino. The halogen represented by $R_2$ may be chlorine, bromine, iodine or fluorine.

The alkyl substituted amino group represented by $R_2$ includes mono- or di-alkyl substituted ones whose alkyl moiety is that having 1 to 3 carbon atoms, e.g. methylamino, ethylamino, propylamino, isopropylamino, dimethylamino, diethylamino or dipropylamino.

In the formula (II), the alkyl group represented by $R'_1$ may be any of straight-chain, branched or cyclic alkyl group having 1 to 6 carbon atoms. Typical examples of the alkyl group may be methyl, ethyl, propyl, isopropyl, butyl, isobutyl, sec.-butyl, tert.-butyl, pentyl, cyclopentyl, hexyl, cyclohexyl, etc. Among them, for practical purposes, lower alkyls having 1 to 3 carbon atoms are preferred.

The alkoxy group represented by $R'_1$ may for example be that having 1 to 4 carbon atoms in the alkyl moieties, such as methoxy, ethoxy, propoxy, isopropoxy, butoxy, etc.

The mono-alkyl substituted amino group represented by $R'_1$ may be that having 1 to 3 carbon atoms in the alkyl moieties, such as methylamino, ethylamino, propylamino or isopropylamino. The alkoxycarbonyl groups $R'_1$ and $R_3$ is represented by the formula —$COOR_4$, wherein $R_4$ is a straight-chain alkyl having 1 to 6 carbon atoms, e.g. methyl, ethyl, n-propyl, n-butyl, n-hexyl, etc.

The alkyl substituted carboxamide group represented by $R_3$ includes mono- or di-alkyl substituted ones whose alkyl moiety is alkyl one having 1 to 3 carbon atoms. Typical examples of these groups may be N-methyl carboxamide, N,N-dimethyl carboxamide, N-ethyl carboxamide, N,N-diethyl carboxamide and N-propyl carboxamide.

The compounds of the formula (I) according to this invention can be prepared by hydrolyzing the compounds of the formula (II). This hydrolysis reaction can be accomplished under acidic or alkaline conditions, the hydrolysis under acid conditions being preferred. Thus, for the purpose, a mineral acid such as hydrochloric acid, sulfuric acid, perchloric acid, phosphoric acid or the like or an organic acid such as trifluoroacetic acid, formic acid, acetic acid or the like may be employed. Generally this reaction is preferably conducted in the presence of water and in a mixture of an organic acid with a mineral acid. While the temperature, time and other conditions of reaction are not particularly critical, the reaction is generally carried out at about 50° to 150° C. for a time varying from about one hour to about 2 days.

The compound of general formula (I) wherein $R_1$ is carboxyl may be converted to a compound wherein $R_1$ is hydrogen by heating the material compound at a temperature slightly higher than the temperature conductive to decarboxylation and in the presence or absence of a solvent.

The compound of general formula (I) can be converted to the corresponding organic amine salts, alkali metal salts or ammonium salts by reacting (I) in the per se conventional manner with an organic amine (e.g. ethanolamine, diethanolamine, dl-methylephedrine, 1-(3,5-dihydroxyphenyl)-L-isopropylaminoethanol, isoproterenol, dextromethorphan, hetrazan (diethylcarbamazine), diethylamine, triethylamine, etc.), an alkali metal hydroxide (e.g. sodium hydroxide, potassium hydroxide, etc.) or ammonia, for example by mixing them together and heating in a suitable solvent.

The resulting compounds (I) or salts have anti-allergic properties and the particular organic amine salts just mentioned have particularly excellent anti-allergic activity, thus being of value as prophylactic and curative drugs for the treatment of allergic asthma, allergic dermatitis, hay fever and other allergic diseases in mammals including human beings. Further, these alkali metal salts and organic amine salts are soluble in water and the resultant aqueous solutions are stable, thus being suitable for the preparation of such dosage forms as injectable solutions and aqueous solutions.

When a compound of general formula (I) or a salt thereof is used for the prevention or treatment of said allergic diseases in adult human, it can be orally administered at the usual dose level of about one to 500 mg/day in such dosage forms as tablets, capsules, powders or solutions, or administered by other routes in such dosage forms as injectable solutions, inhalations, ointments, etc.

The starting compounds of the formula (II) can be produced by the following procedure. Thus, the compound of the formula (III):

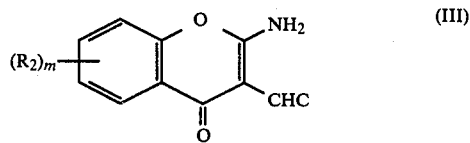

wherein m and $R_2$ have the same meaning as defined above, can be produced by reacting a compound of general formula (IV):

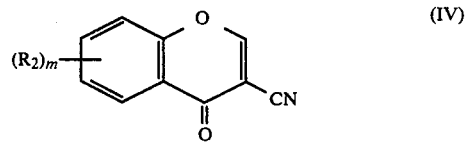

(wherein m and $R_2$ have the same meaning as defined above), which is obtainable by the process described in U.S. Pat. No. 3,896,114, with water in the presence of a base. As the base may be mentioned organic amines such as primary amines (e.g. ethylamine, n-propylamine, n-butylamine, benzylamine, aniline, etc.), secondary amines (e.g. dimethylamine, diethylamine, dipropylamine, dibutylamine, piperidine, pyrrolidine, etc.), tertiary amines (e.g. triethylamine, etc.), heterocyclic bases (e.g. imidazole, 2-methylimidazole, morpholine, etc.), and inorganic bases such as aqueous ammonia, ammonium acetate, ammonium carbonate, sodium acetate, sodium carbonate, sodium hydrogen carbonate, etc. The amount of such base is not particularly critical and may range from a catalytic amount to a large excess.

Generally the reaction is preferably conducted in a solvent miscible with water. As examples of the solvent may be mentioned dimethylformamide, dimethylsulfoxide, hexamethylphosphoric acid triamide, organic acids (e.g. formic acid, acetic acid, propionic acid, etc.) and ethers (e.g. tetrahydrofuran, dioxane, etc.). While the temperature, time and other conditions of the reaction are not particularly critical, the reaction is generally carried out at room temperature to about 100° C. for a time varying from a few minutes to about 3 hours.

A compound of the formula (II) may be produced by reacting a compound of the formula (III) with an active methylene compound, an acetylene-carboxylic acid derivative in an organic solvent or a cyanoacetyl halide in the presence of a substituted formamide.

As examples of the active methylene compound to be employed in the reaction, there may be mentioned methyl acetoacetate, ethyl acetoacetate, methyl cyanoacetate, ethyl cyanoacetate, cyanoacetamide, malononitrile, ethyl oxaloacetate, diethyl malonate, dimethyl malonate, ethyl benzoylacetate, methyl 3-oxo-n-caproate, etc. Normally for practical purposes, about 1 to 10 molar equivalents of the active methylene compound is employed to each molar equivalent of the compound (III).

The above reaction is preferably conducted in the presence of a base which may be an organic amine. The organic amine may be a primary amine such as n-butylamine, benzylamine, aniline, etc.; a secondary amine such as diethylamine, dipropylamine, dibutylamine, piperidine, pyrrolidine, etc.; a tertiary amine such as 1,8-diazabicyclo-(5,4,0)-7-undecene, triethylamine, etc.; or a heterocyclic base such as imidazole, 2-methylimidazole, morpholine, etc. The proportion of the organic base is normally from a catalytic amount to about 5 molar equivalents per mole of compound (III).

Generally the reaction is desirably conducted in an organic solvent. As examples of the solvent may be mentioned alcohols such as methanol, ethanol, propanol, butanol, etc.; aromatic hydrocarbons such as benzene, toluene, etc.; and dimethylformamide. Although the reaction temperature, time and other conditions are virtually optional, it is generally desirable to conduct the reaction at a temperature somewhere between room temperature and near the boiling point of the solvent used for about one to 24 hours.

The invention may be practiced by the following procedure as well. Thus, a compound of general formula (III) is reacted with an acetylene-carboxylic acid derivative. As examples of the acetylene-carboxylic acid derivative, there may be mentioned dimethyl acetylenedicarboxylate, diethyl acetylenedicarboxylate, methyl propiolate, ethyl propiolate, cyanoacetylene, etc. Where a propiolic acid ester is employed, the intermediate aminoacrylate derivative may be isolated or may be further subjected to cyclization reaction. The acetylenedicarboxylic acid derivative may be used, normally and practically, in a proportion of about one to 10 molar equivalents per mole of compound (III).

Generally the above reaction is desirably conducted in the presence of a base which may be an organic amine. As examples of such organic amine may be mentioned tertiary amines such as triethylamine, tripropylamine, tributylamine, etc.; heterocyclic amines such as pyridine, quinoline, imidazole, 2-methylimidazole, morpholine, etc.; and secondary amines such as piperidine, pyrrolidine, diethylamine, dipropylamine, dibutylamine, etc. Theorganic base is normally employed in a proportion from a catalytic amount to about 10 molar equivalents per mole of starting compound (II).

Generally speaking, this reaction is desirably conducted in an organic solvent. As examples of the solvent may be mentioned alcohols such as methanol, ethanol, propanol, butanol, etc. aromatic hydrocarbons such as benzene, toluene, xylene, etc.; dimethylformamide; and so forth. While the temperature, time and other conditions of the reaction are not particularly critical, the reaction is generally conducted at a temperature somewhere between room temperature and near the boiling point of the solvent employed for a time ranging from about one to 24 hours.

The compound of the general formula (II) according to this invention can be produced by the following process. Thus, compound (II) is produced by reacting a compound of the general formula (III) with a cyanoacetyl halide in the presence of a substituted formamide. The cyanoacetyl halide employed in this reaction may for example be cyanoacetyl chloride, cyanoacetyl bromide, cyanoacetyl iodide, cyanoacetyl fluoride or the like. The substituted formamide used in this reaction may be alkyl or arylsubstituted formamide, such as N,N-dimethylformamide, N,N-diethylformamide, N,N-dipropylformamide, N-methyl-N-ethylformamide, N-methyl-N-phenylformamide, N,N-diphenylformamide or the like. This reaction may be conducted in the presence of such a substituted formamide alone, i.e. using it as the reaction solvent, although the reaction may be carried out, if required, in a solvent mixture of said substituted formamide with an extraneous solvent that will not interfere with the reaction. The solvent just mentioned is preferably one of the common organic solvents such as hydrocarbons (e.g. benzene, toluene, xylene, petroleum ether, etc.), ethers (e.g. tetrahydrofuran, dioxane, ethyl ether, ethylene glycol dimethylether, etc.), halogenated hydrocarbons (e.g. chloroform, dichloromethane, dichloroethane, tetrachloroethane, etc.), esters (e.g. ethyl acetate, methyl acetate, butyl acetate, etc.), acetonitrile, dimethylsulfoxide and so forth. The proportion of cyanoacetyl halide used in the production of compound (II) is normally in the range of about 1 to 10 molar equivalents based on starting compound (III). While the temperature, time and other conditions of reaction are not particularly critical, the reaction is normally carried out at about 20° to about 120° C. for about 30 minutes to about 2 days. The proportion of said substituted formamide is not particularly critical, either. It is, however, used in a proportion of about 2 or more molar equivalents based on starting compound (III).

A compound (II) wherein $R'_1$ is alkoxy may be produced by, for example, reacting a compound (II) wherein $R'_1$ is hydroxy with diazomethane or an alkyl halide such as methyl iodide, ethyl iodide, propyl iodide, isopropyl iodide, butyl iodide, isobutyl iodide, etc. in the presence of a base (e.g. potassium carbonate).

This reaction is desirably connected in an organic solvent such as chloroform, dichloromethane, acetone, methyl ethyl ketone, etc. The above reaction is general conducted at a temperature between 0° C. and near the boiling point of the solvent employed for about several minutes to a few hours.

A compound (II) wherein $R'_1$ is monoalkylamino may be for example produced by the following procedure. Thus, it can be produced by reacting a compound (II) wherein $R'_1$ is chlorine, which is obtainable by reacting a compound (II) wherein $R'_1$ is hydroxy with a mixture of phosphoryl trichloride and phosphorus pentachloride at about 100° to 120° C. for a time varying from several hours to a few days, with a monoalkylamine such as methylamine, ethylamine, propylamine, etc. Generally the reaction is conducted in an organic solvent. As example of the solvent for dissolving the compound (II) wherein $R'_1$ is chlorine may be mentioned chloroform, dichloromethane, etc. and as the solvent for dissolving monoalkylamine is exemplified methanol, ethanol, propanol, chloroform, etc.

While the temperature, time and other conditions of the reaction of a compound (II) wherein $R'_1$ is chlorine and monoalkylamine are not particularly critical, the reaction is generally carried out at about 0° C. to room temperature for a few minutes to about 3 hours.

A compound (II) wherein $R'_1$ is hydroxy may be for example produced by reacting a compound (II) wherein $R'_1$ is amino with an alkali salt of nitrile (e.g. sodium nitrate, potassium nitrite, etc.) in an aqueous inorganic or organic acid (e.g. hydrochloric acid, acetic acid, etc.).

REFERENCE EXAMPLE 1

A mixture of 2 ml of morpholine, 3 ml of dimethylformamide and 10 ml of water was heated to 60° C. and, under stirring, 1.71 g of finely divided 4-oxo-4H-1-benzopyran-3-carbonitrile was added over a period of 5 minutes. The mixture was heated at that temperature for one hour and the resultant precipitate was recovered by filtration, rinsed with water, recrystallized from acetic acid and washed with chloroform. By the above procedure was obtained 1.32 g crystals of 2-amino-4-oxo-4H-1-benzopyran-3-carboxaldehyde melting at 252°–255° C. (decomp.).

Nuclear magnetic resonance spectrum (DMSO-$d_6$) δ: 10.19(1H, s), 9.67(ca 1.5H, br. s), 8.11(1H, dd, J=2&8 Hz), 7.97-7.30(3H, m)

Elemental analysis, for $C_{10}H_7NO_3$: Calcd.: C, 63.49; H, 3.73; N, 7.41. Found: C, 63.59; H, 3.44; N, 7.45.

By procedures similar to the above, the following compounds were produced.

| Starting compound | Product | m.p. °(C.)/ Recrys. solvent |
|---|---|---|
| 6-Methyl-4-oxo-4H-1-benzopyran-3-carbonitrile | 2-Amino-6-methyl-4-oxo-4H-1-benzopyran-3-carboxaldehyde | 282–284 (decomp.) Acetic acid |
| 6-Ethyl-4-oxo-4H-1-benzopyran-3-carbonitrile | 2-Amino-6-ethyl-4-oxo-4H-1-benzopyran-3-carboxaldehyde | 246–249 (decomp.) Acetone |
| 6-Chloro-4-oxo-4H-1-benzopyran-3-carbonitrile | 2-Amino-6-chloro-4-oxo-4H-1-benzopyran-3-carboxaldehyde | 308–310 (decomp.) Acetic acid |
| 6-Methoxy-4-oxo-4H-1-benzopyran-3-carbonitrile | 2-Amino-6-methoxy-4-oxo-4H-1-benzopyran-3-carboxaldehyde | 251–254 (decomp.) Chloroform |
| 6,8-Dimethyl-4-oxo-4H-1-benzopyran-3-carbonitrile | 2-Amino-6,8-dimethyl-4-oxo-4H-1-benzopyran-3-carboxaldehyde | 259–263 (decomp.) Acetic acid |
| 7-Hydroxy-4-oxo-4H-1-benzopyran-3-carbonitrile | 2-Amino-7-hydroxy-4-oxo-4H-1-benzopyran-3-carboxaldehyde | 297–300 (decomp.) Acetic acid |
| 6-Nitro-4-oxo-4H-1-benzopyran-3-carbonitrile | 2-Amino-6-nitro-4-oxo-4H-1-benzopyran-3-carboxaldehyde | 290–293 (decomp.) Formic acid |
| 6-Isopropyl-4-oxo-4H-1-benzopyran-3-carbonitrile | 2-Amino-6-isopropyl-4-oxo-4H-1-benzopyran-3-carboxaldehyde | 206–208 Acetic acid |
| 6-n-Butyl-4-oxo-4H-1-benzopyran-3-carbonitrile | 2-Amino-6-n-butyl-4-oxo-4H-1-benzopyran-3-carboxaldehyde | 220–222 Acetic acid |
| 8-Methoxy-4-oxo-4H-1-benzopyran-3-carbonitrile | 2-Amino-8-methoxy-4-oxo-4H-1-benzopyran-3-carboxaldehyde | 235–238 Chloroform |
| 3-Cyano-benzo(f)-chromone | 2-Amino-benzo(f)-chromone-3-carboxaldehyde | 258–260 (decomp. with foaming) Acetic acid |
| 6-Dimethylamino-4-oxo-4H-benzopyran-3-carbonitrile | 2-Amino-6-dimethyl-amino-4-oxo-4H-1-benzopyran-3-carboxaldehyde | 276–280 (decomp.) Chloroform-Methanol |
| 6-tert.-Butyl-4-oxo-4H-1-benzopyran-3-carbonitrile | 2-Amino-6-tert.-butyl-4-oxo-4H-1-benzopyran-3-carboxaldehyde | 240–242 Acetic acid |

REFERENCE EXAMPLE 2

A mixture of 2.17 g of 2-amino-6-ethyl-4-oxo-4H-1-benzopyran-3-carboxaldehyde, 4.0 ml of ethyl acetoacetate, 50 ml of ethanol and 5 ml of piperidine was refluxed under stirring for 2 hours. After cooling, the precipitate was recovered by filtration and recrystallized from ethanol. By this procedure was obtained 1.60 g yellow needles of ethyl 7-ethyl-2-methyl-1-azaxanthone-3-carboxylate melting at 149°–151° C.

Infrared absorption spectrum (Nujol)cm$^{-1}$: 1715, 1655

Nuclear magnetic resonance spectrum (CDCl$_3$) δ: 9.15(1H, s), 8.09(1H, s), 7.37–7.75(2H, m), 4.44(2H, q, J=7 Hz), 2.97(3H, s), 2.81(2H, q, J=7 Hz), 1.45(3H, t, J=7 Hz), 1.33(3H, t, J=7 Hz)

Elemental analysis, for C$_{18}$H$_{17}$NO$_4$: Calcd.: C, 69.44; H, 5.50; N, 4.50. Found: C, 69.58; H, 5.44; N, 4.28.

The following compounds were produced by procedures similar to the above.

| Starting compound | Product | m.p. (°C.)/ Recrys. solvent |
|---|---|---|
| 2-Amino-4-oxo-4H-1-benzopyran-3-carboxaldehyde | Ethyl 2-methyl-1-azaxanthone-3-carboxylate | 155–156 Ethanol |
| 2-Amino-6-methoxy-4-oxo-4H-1-benzopyran-3-carboxaldehyde | Ethyl 7-methoxy-2-methyl-1-azaxanthone-3-carboxylate | 203–205 Ethanol |
| 2-Amino-6,8-dimethyl-4-oxo-4H-1-benzopyran-3-carboxaldehyde | Ethyl 7,9-dimethyl-2-methyl-1-azaxanthone-3-carboxylate | 165–166 Ethanol |
| 2-Amino-6-chloro-4-oxo-4H-1-benzopyran-3-carboxaldehyde | Ethyl 7-chloro-2-methyl-1-azaxanthone-3-carboxylate | 175–176 Ethyl acetate |
| 2-Amino-6-nitro-4-oxo-4H-1-benzopyran-3-carboxaldehyde | Ethyl 7-nitro-2-methyl-1-azaxanthone-3-carboxylate | 212–213 Dimethylformamide |

REFERENCE EXAMPLE 3

A mixture of 2.17 g of 2-amino-6-ethyl-4-oxo-4H-1-benzopyran-3-carboxaldehyde, 4.0 ml of ethyl cyanoacetate, 50 ml of ethanol and 5.0 ml of piperidine was refluxed for 30 minutes and, after cooling, the crystalline precipitate was recovered by filtration and washed with chloroform. By the above procedure was obtained 2.07 g of colorless needles of ethyl 2-amino-7-ethyl-1-azaxanthone-3-carboxylate, melting at 279°–280° C.

Elemental analysis, for C$_{17}$H$_{16}$N$_2$O$_4$: Calcd.: C, 65.37; H, 5.16; N, 8.97. Found: C, 65.24; H, 5.08; N, 8.86.

The following compounds were produced by procedures similar to the above.

| Starting compound | Product | m.p. (°C.)/ Recrys. solvent |
|---|---|---|
| 2-Amino-4-oxo-4H-1-benzopyran-3-carboxaldehyde | Ethyl 2-amino-1-azaxanthone-3-carboxylate | 241–242 Chloroform-ethanol |
| 2-Amino-6-methoxy-4-oxo-4H-1-benzopyran-3-carboxaldehyde | Ethyl 2-amino-7-methoxy-1-azaxanthone-3-carboxylate | 285–286 Chloroform-ethanol |
| 2-Amino-6,8-dimethyl-4-oxo-4H-1-benzopyran-3-carboxaldehyde | Ethyl 2-amino-7,9-dimethyl-1-azaxanthone-3-carboxylate | 299–300 Chloroform-ethanol |
| 2-Amino-6-chloro-4-oxo-4H-1-benzopyran-3-carboxaldehyde | Ethyl 2-amino-7-chloro-1-azaxanthone-3-carboxylate | 299–300 Dimethylformamide |
| 2-Amino-6-methyl-4-oxo-4H-1-benzopyran-3-carboxaldehyde | Ethyl 2-amino-7-methyl-1-azaxanthone-3-carboxylate | 277–279 Chloroform |
| 2-Amino-6-isopropyl-4-oxo-4H-1-benzopyran-3-carboxaldehyde | Ethyl 2-amino-7-isopropyl-1-azaxanthone-3-carboxylate | 243–244 Ethanol |
| 2-Amino-8-methoxy-4-oxo-4H-benzopyran-3-carboxaldehyde | Ethyl 2-amino-9-methoxy-1-azaxanthone-3-carboxylate | >300 Dimethylformamide |
| 2-Amino-6-n-butyl-4-oxo-4H-1-benzopyran-3-carboxaldehyde | Ethyl 2-amino-7-n-butyl-1-azaxanthone-3-carboxylate | 234.5–235 Ethanol |
| 2-Amino-benzo(f)-chromone-3-carboxaldehyde | Ethyl 2-amino-benzo-(h)-1-azaxanthone-3-carboxylate | 279–280 Chloroform-ethanol |
| 2-Amino-7-hydroxy-4-oxo-4H-1-benzopyran-3-carboxaldehyde | Ethyl 2-amino-8-hydroxy-1-azaxanthone-3-carboxylate | >300 Dimethylformamide |
| 2-Amino-6-methoxy-4-oxo-4H-1-benzopyran-3-carboxaldehyde | Ethyl 2-amino-7-methoxy-1-azaxanthone-3-carboxylate | 286–288 Chloroform-ethanol |

REFERENCE EXAMPLE 4

A mixture of 366 mg of 2-amino-4-oxo-4H-1-benzopyran-3-carboxaldehyde, 500 mg of methyl 3-oxo-n-caproate and 0.6 ml of piperidine in 20 ml of methanol was refluxed for 6 hours. The reaction mixture was concentrated under reduced pressure and the residue was chromatographed on a column of silica gel. Elution was carried out with chloroform and the leading eluate was collected and recrystallized from methanol. By the above procedure was obtained 52 mg yellow crystals of methyl 2-n-propyl-1-azaxanthone-3-carboxylate melting at 105°–106° C.

Infrared absorption spectrum (KBr) cm$^{-1}$: 1725, 1680

Nuclear magnetic resonance spectrum (CDCl$_3$) δ: 9.23(1H, s), 8.35(1H, dd, J=8 & 2 Hz), 7.3–8.0(3H, m), 3.95(3H, s), 3.32(2H, t, J=7 Hz), 1.6–2.3(2H, m), 1.06(3H, t, J=7 Hz)

Elemental analysis, for C$_{17}$H$_{15}$NO$_4$: Calcd.: C, 68.67; H, 5.08; N, 4.71. Found: C, 68.79; H, 5.02; N, 4.62.

REFERENCE EXAMPLE 5

A mixture of 1.085 g of 2-amino-6-ethyl-4-oxo-4H-1-benzopyran-3-carboxaldehyde, 2.0 ml of ethyl benzoylacetate, 50 ml of ethanol and 1.0 ml of piperidine was refluxed under stirring for 6 hours and, while hot, the small amount of insolubles was filtered off. The filtrate was cooled and the resultant precipitate was recovered by filtration and recrystallized from ethanol. By the above procedure was obtained 635 mg of ethyl 7-ethyl-2-phenyl-1-azaxanthone-3-carboxylate as pale yellow needles melting at 176°–177° C.

Infrared absorption spectrum (Nujol) cm$^{-1}$: 1730, 1675

Nuclear magnetic resonance spectrum (CDCl$_3$) δ: 9.12(1H, s), 8.18(1H, s), 7.30–7.87(7H, m), 4.28(2H, q, J=7 Hz, 2.82(2H, q, J=7 Hz), 1.03–1.53(6H, t+t), Elemental analysis, for C$_{23}$H$_{19}$NO$_4$: Calcd.: C, 73.98; H, 5.13; N, 3.75. Found: C, 74.10; H, 5.08; N, 3.71.

REFERENCE EXAMPLE 6

A mixture of 217 mg of 2-amino-6-ethyl-4-oxo-4H-1-benzopyran-3-carboxaldehyde, 300 mg of cyanoacetamide, 5 ml of ethanol and 0.5 ml of piperidine was refluxed under stirring for one hour and, after cooling, the sparingly soluble product was collected by filtration and recrystallized from dimethylformamide-acetone. By the above procedure was obtained 180 mg crystals of 2-amino-7-ethyl-1-azaxanthone-3-carboxamide. m.p. > 300° C.

Nuclear magnetic resonance spectrum ($CF_3COOD$) δ: 9.50(1H, s), 8.20(1H, d, J=2 Hz), 7.88(1H, dd), 7.63(1H, d, J=9 Hz), 2.91(2H, q, J=7 Hz), 1.38(3H, t, J=7 Hz)

Elemental analysis, for $C_{15}H_{13}N_3O_3$: Calcd.: C, 63.59; H, 4.63; N, 14.33. Found: C, 63.40; H, 4.72; N, 14.79.

The following compounds were produced by procedures similar to that described above.

| Starting compound | Product | m.p. (°C.)/ Recrys. solvent |
|---|---|---|
| 2-Amino-4-oxo-4H-1-benzopyran-3-carboxaldehyde | 2-Amino-1-azaxanthone-3-carboxamide | >300, Dimethylformamide |
| 2-Amino-6-chloro-4H-1-benzopyran-3-carboxaldehyde | 2-Amino-7-chloro-1-azaxanthone-3-carboxamide | >300, Dimethylformamide |

REFERENCE EXAMPLE 7

A mixture of 217 mg of 2-amino-6-ethyl-4-oxo-4H-1-benzopyran-3-carboxaldehyde, 300 mg of malononitrile, 5 ml of ethanol and 0.5 ml of piperidine was stirred under reflux for 15 minutes and, after cooling, the sparingly soluble product was collected by filtration and recrystallized from dimethylformamide. By the above procedure was obtained 160 mg of 2-amino-7-ethyl-1-azaxanthone-3-carbonitrile as colorless needles, m.p. > 300° C.

Infrared absorption spectrum (Nujol) $cm^{-1}$: 3325, 3125, 2225, 1660

Nuclear magnetic resonance spectrum ($CF_3COOD$) δ: 9.07(1H, s), 8.16(1H, d, J=2 Hz), 7.88(1H, dd), 7.63 (1H, d, J=9 Hz), 2.92(2H, q, J=7 Hz), 1.39(3H, t, J=7 Hz)

Elemental analysis, for $C_{15}H_{11}N_3O_2$: Calcd.: C, 67.91; H, 4.18; N, 15.84. Found: C, 67.75; H, 4.01; N, 16.00.

The following compounds were produced by procedures similar to that described above.

| Starting compound | Product | m.p. (°C.)/ Recrys. solvent |
|---|---|---|
| 2-Amino-4-oxo-4H-1-benzopyran-3-carboxaldehyde | 2-Amino-1-azaxanthone-3-carbonitrile | >300 Dimethylformamide |
| 2-Amino-6-chloro-4-oxo-4H-1-benzopyran-3-carboxaldehyde | 2-Amino-7-chloro-1-azaxanthone-3-carbonitrile | >300 Dimethylformamide |
| 2-Amino-6-dimethylamino-4-oxo-4H-1-benzopyran-3-carboxaldehyde | 2-Amino-7-dimethylamino-1-azaxanthone-3-carbonitrile | >300 Ethanol |
| 2-Amino-6-isopropyl-4-oxo-4H-1-benzopyran-3-carboxaldehyde | 7-Isopropyl-2-amino-3-cyano-1-azaxanthone | >300 Dimethylformamide |
| 2-Amino-6-methyl-4-oxo-4H-1-benzopyran-3-carboxaldehyde | 7-Methyl-2-amino-3-cyano-1-azaxanthone | >300 Dimethylformamide |

REFERENCE EXAMPLE 8

A mixture of 2.17 g of 2-amino-6-ethyl-4-oxo-4H-1-benzopyran-3-carboxaldehyde, 1.778 g of dimethyl acetylenedicarboxylate, 50 ml of methanol and 0.5 ml of triethylamine was stirred under reflux for 3 hours and, after cooling, the precipitate was collected by filtration. The precipitate was added to chloroform and, after stirring, the sparingly soluble product was filtered off. The filtrate was concentrated to dryness and dissolved in about 50 ml of n-hexane-chloroform-acetone (10:5:0.5). The solution was run onto a column of silica gel (30 g) and elution was carried out with the same solvent system. The eluate was concentrated and the residue was recrystallized from methanol. By the above procedure was obtained 590 mg of dimethyl 7-ethyl-1-azaxanthone-2,3-dicarboxylate as colorless needles melting at 169°-170° C.

Infrared absorption spectrum (Nujol) $cm^{-1}$: 1745, 1720, 1670

Nuclear magnetic resonance spectrum ($CDCl_3$) δ: 9.20(1H, s), 8.10(1H, d, J=2 Hz), 7.68(1H, dd, J=2 & 8 Hz), 7.52(1H, d, J=8 Hz), 4.05(3H, s), 3.99(3H, s), 2.83(2H, q, J=7 Hz), 1.33(3H, t, J=7 Hz)

Elemental analysis, for $C_{18}H_{15}NO_6$: Calcd.: C, 63.34; H, 4.43; N, 4.10. Found: C, 63.15; H, 4.30; N, 4.01.

REFERENCE EXAMPLE 9

A mixture of 1.83 g of 2-amino-4-oxo-4H-1-benzopyran-3-carboxaldehyde, 1.6 g of dimethyl acetylenedicarboxylate, 50 ml of ethanol and 1 drop of triethylamine was stirred under reflux for 2 hours. The reaction mixture was concentrated under reduced pressure and ether was added to the residue. The crystalline product was collected by filtration, washed with ether and recrystallized from methanol. By the above procedure was obtained 2.06 g of dimethyl 1-azaxanthone-2,3-dicarboxylate as colorless needles melting at 149°-151° C.

Infrared absorption spectrum (KBr) $cm^{-1}$: 1750, 1730, 1675

Nuclear magnetic resonance spectrum ($CDCl_3$) δ: 9.28(1H, s), 8.20(1H, dd, J=2 & 8 Hz), 7.4-8.0 (3H, m), 4.06(3H, s), 4.02(3H, s)

Elemental analysis, for $C_{16}H_{11}NO_6$: Calcd.: C, 55.34; H, 2.90; N, 4.03. Found: C, 55.25; H, 2.74; N, 3.94.

REFERENCE EXAMPLE 10

A mixture of 2.17 g of 2-amino-6-ethyl-4-oxo-4H-1-benzopyran-3carboxaldehyde, 2.55 g of diethyl acetylenedicarboxylate, 50 ml of ethanol and 0.5 ml of triethylamine was refluxed for 2 hours and, while hot, the small amount of sparingly soluble product was filtered off. The filtrate was cooled and the resultant crystals were collected by filtration and recrystallized from ethanol. By the above procedure was obtained 3.2 g of diethyl 7-ethyl-1-azaxanthone-2,3-dicarboxylate as colorless crystals melting at 112°-113° C.

Infrared absorption spectrum (Nujol) $cm^{-1}$: 1745, 1718, 1665

Nuclear magnetic resonance spectrum ($CDCl_3$) δ: 9.28(1H, s), 8.13(1H, s), 7.43-7.83(2H, m), 4.27-4.77 (4H, q+q), 2.82(2H, q, J=7 Hz), 1.17-1.62(9H)

Elemental analysis, for $C_{20}H_{19}NO_6$: Calcd.: C, 65.03; H, 5.19; N, 3.79. Found: C, 65.26; H, 5.02; N, 3.87.

REFERENCE EXAMPLE 11

A mixture of 217 mg of 2-amino-6,8-dimethyl-4-oxo-4H-1-benzopyran-3-carboxaldehyde, 255 mg of diethyl acetylenedicarboxylate, 10 ml of ethanol and 0.05 ml of triethylamine was refluxed for 3 hours, followed by addition of 150 mg of diethyl acetylenedicarboxylate, 1 ml of ethanol and 2 drops of triethylamine. The mixture was further refluxed for 2 hours. After cooling, the precipitate was collected by filtration and recrystallized twice from ethanol. By the above procedure was obtained 260 mg of diethyl 7,9-dimethyl-1-azaxanthone-2,3-dicarboxylate as yellow crystals melting at 156°–159° C.

Infrared absorption spectrum (Nujol) cm$^{-1}$: 1740, 1725, 1675

Nuclear magnetic resonance spectrum (CDCl$_3$) δ: 9.22(1H, s), 7.90(1H, s), 7.45(1H, s), 4.57(2H, q, J=7 Hz), 4.45(2H, q, J=7 Hz), 2.58(3H, s), 2.43(3H, s), 1.47(6H, t, J=7 Hz).

REFERENCE EXAMPLE 12

By a procedure similar to that described in Reference Example 9, dimethyl 7-chloro-1-azaxanthone-2,3-dicarboxylate was produced from 2-amino-6-chloro-4-oxo-4H-1-benzopyran-3-carboxaldehyde. Light-yellow needles (recrys. solvent: ethyl acetate), m.p. 220°–223° C.

Elemental analysis, for C$_{16}$H$_{10}$NO$_6$Cl: Calcd. C, 55.34; H, 2.90; N, 4.03. Found: C, 55.25; H, 2.74; N, 3.94.

REFERENCE EXAMPLE 13

A mixture of 5.5 g of 2-amino-4-oxo-4H-1-benzopyran-3-carboxaldehyde, 5 g of ethyl propiolate, 25 ml of dimethylformamide and 0.1 ml of triethylamine was heated under stirring at 90° C. for one hour. The reaction mixture was concentrated under reduced pressure and the residue was recrystallized from methanol. By the above procedure was obtained 3.5 g of ethyl 3-N-(3-formyl-4-oxo-4H-1-benzopyran-2-yl)aminoacrylate as colorless needles melting at 201°–203° C.

Infrared absorption spectrum (KBr) cm$^{-1}$: 1700, 1680

Nuclear magnetic resonance spectrum (CDCl$_3$) δ: 10.47(1H, s), 8.23(1H, dd, J=2 & 8 Hz), 7.68(1H, d, J=9 Hz), 7.3–7.8(3H, m), 5.45(1H, d, J=9 Hz), 4.38(2H, q, J=6 Hz), 3.66(3H, t, J=6 Hz)

Elemental analysis, for C$_{15}$H$_{13}$NO$_5$: Calcd.: C, 62.71; H, 4.56; N, 4.88. Found: C, 62.47; H, 4.40; N, 4.81.

Then, a mixture consisting of 3.5 g of the above ethyl 3-N-(3-formyl-4-oxo-4H-1-benzopyran-2-yl)aminoacrylate, 5 ml of triethylamine and 20 ml of toluene was refluxed for 24 hours. The reaction mixture was concentrated under reduced pressure and the residue was recrystallized from methanol. By the above procedure was obtained 1.42 g of ethyl 1-azaxanthone-3-carboxylate as light-yellow crystals melting at 139°–140° C.

Infrared absorption spectrum (KBr) cm$^{-1}$: 1715, 1670, 1615

Nuclear magnetic resonance spectrum (CDCl$_3$) δ: 9.2–9.4(2H, m), 8.35(1H, dd, J=2 & 7 Hz), 7.3–8.0(3H, m), 4.50(2H, q, J=8 Hz), 1.34(3H, t, J=8 Hz)

Elemental analysis, for C$_{15}$H$_{11}$NO$_4$: Calcd.: C, 66.91; H, 4.12; N, 5.20. Found: C, 66.71; H, 4.00; N, 5.11.

REFERENCE EXAMPLE 14

A mixture of 2.23 g of 2-amino-6-chloro-4-oxo-4H-1-benzopyran-3-carboxaldehyde, 5 g of ethyl propiolate, 30 ml of dimethylformamide and 0.1 ml of triethylamine was stirred at 90° C. for one hour and, after cooling, filtered to recover the precipitate. The precipitate was washed with methanol, whereby 1.6 g of ethyl 3-N-(3-formyl-6-chloro-4-oxo-4H-1-benzopyran-2-yl)aminoacrylate was obtained as crude crystals. The crystals were stirred with 15 ml of dimethylformamide and 5 ml of triethylamine under heating at 130°–140° C. for 2 hours. The reaction mixture was concentrated under reduced pressure and the residue was recrystallized from ethanol. By the above procedure was obtained 650 mg of ethyl 7-chloro-1-azaxanthone-3-carboxylate as light-yellow needles melting at 176°–177° C.

Infrared absorption spectrum (KBr) cm$^{-1}$: 1725, 1675

Nuclear magnetic resonance spectrum (CDCl$_3$) δ: 9.37(1H, d, J=2 Hz), 9.27(1H, d, J=2 Hz), 8.30(1H, d, J=2 Hz), 7.80(1H, dd, J=2 & 8 Hz), 7.60(1H, d, J=8 Hz), 4.84(2H, q, J=7 Hz), 1.43(3H, t, J=7 Hz)

Elemental analysis, for C$_{15}$H$_{10}$NO$_4$Cl: Calcd.: C, 59.32; H, 3.32; N, 4.61. Found: C, 59.40; H, 3.18; N, 4.44.

REFERENCE EXAMPLE 15

By a procedure similar to that described in Reference Example 9, ethyl 7-nitro-1-azaxanthone-3-carboxylate was produced from 2-amino-6-nitro-4-oxo-4H-1-benzopyran-3-carboxaldehyde. Light-yellow platelets (as recrystallized from dimethylformamide), m.p. 228°–229° C.

Infrared absorption spectrum (KBr) cm$^{-1}$: 1720, 1675

Nuclear magnetic resonance spectrum (CF$_3$CO$_2$D) δ: 9.1–9.3(2H, br. s.), 8.92(1H, d, J=2 Hz), 8.42(1H, dd, J=2 & 9 Hz), 7.48(1H, d, J=9 Hz), 4.22(2H, q, J=7 Hz), 1.10(3H, t, J=7 Hz)

Elemental analysis, for C$_{15}$H$_{10}$N$_2$O$_6$: Calcd.: C, 57.33; H, 3.21; N, 8.92. Found: C, 56.96; H, 3.09; N, 8.76.

REFERENCE EXAMPLE 16

A mixture consisting of 3.17 g of 2-amino-6-ethyl-4-oxo-4H-1-benzopyran-3-carboxaldehyde, 8 g of diethyl malonate, 15 ml of pyridine, 1 ml of 1,8-diazabicyclo[5,4,0]-7-undecene and 50 ml of ethanol was stirred under reflux for 15 hours. The reaction mixture was concentrated under reduced pressure and the residue was made acidic by the addition of dilute hydrochloric acid. The precipitate was recovered by filtration, rinsed with water and recrystallized from ethanol. By the above procedure was obtained 1.23 g of ethyl 7-ethyl-2-hydroxy-1-azaxanthone-3-carboxylate as light-yellow needles melting at 200°–204° C.

Infrared absorption spectrum (KBr) cm$^{-1}$: 1675, 1610

Nuclear magnetic resonance spectrum (CDCl$_3$) δ: 1.35(3H, t, J=7 Hz), 1.53(3H, t, J=7 Hz), 2.87(2H, q, J=7 Hz), 4.58(2H, q, J=7 Hz), 7.4–7.8(2H), 8.23(1H, q, J=2 Hz), 9.30(1H, s)

By procedures similar to the above, the following compounds were produced.

| Starting compound | Product | m.p. (°C.)/ Recrys. solvent |
|---|---|---|
| 2-Amino-6-methyl-4-oxo-4H-1-benzopyran-3-carboxaldehyde | Ethyl 7-methyl-2-hydroxy-1-azaxanthone-3-carboxylate | 221–222 Ethanol |
| 2-Amino-6-methoxy-4-oxo-4H-1-benzopyran-3-carboxaldehyde | Ethyl 7-methoxy-2-hydroxy-1-azaxanthone-3-carboxylate | 269–270 Chloroform-ethanol |

-continued

| Starting compound | Product | m.p. (°C.)/ Recrys. solvent |
|---|---|---|
| 2-Amino-6-n-butyl-4-oxo-4H-1-benzopyran-3-carboxaldehyde | Ethyl 7-n-butyl-2-hydroxy-1-azaxanthone-3-carboxylate | 142–144 Ethanol |
| 2-Amino-8-methoxy-4-oxo-4H-1-benzopyran-3-carboxaldehyde | Ethyl 9-methoxy-2-hydroxy-1-azaxanthone-3-carboxylate | 252–254 Dimethylformamide |

REFERENCE EXAMPLE 17

A mixture consisting of 326 mg of 2-amino-6,8-dimethyl-4-oxo-4H-1-benzopyran-3-carboxaldehyde, 7.5 ml of ethanol, 2.0 ml of pyridine, 2.0 ml of diethyl malonate and 0.1 ml of 1,8-diazabicyclo[5,4,0]-7-undecene was refluxed for 4 hours, at the end of which the solvent was distilled off. To the residue was added 1 N-hydrochloric acid and the sparingly soluble product was collected by filtration and dissolved in chloroform. The chloroform solution was chromatographed on silica gel and elution was carried out with chloroform-acetone-formic acid (9:1:0.1). The purified product was further recrystallized from ethanol to obtain 20 mg pale yellow crystals of ethyl 2-hydroxy-7,9-dimethyl-1-azaxanthone-3-carboxylate, m.p. 251°–253° C.

Infrared absorption spectrum (Nujol) cm$^{-1}$: 1700, 1675, 1650

Nuclear magnetic resonance spectrum (CDCl$_3$) δ: 12.30(1H, br.), 9.22(1H, s), 7.93(1H, s), 7.45(1H, s), 4.55(2H, q, J=7 Hz), 2.57(3H, s), 2.43(3H, s), 1.50 (3H, t)

REFERENCE EXAMPLE 18

In 40 ml of dimethylformamide was dissolved 1.82 g of 2-amino-6-ethyl-4-oxo-4H-1-benzopyran-3-carboxaldehyde, followed by the addition of 3.5 g of cyanoacetyl chloride. The mixture was reacted at 60° C. for 3 hours, with constant stirring. The solvent was then distilled off under reduced pressure and the residue was chromatographed on silica gel. The desired product was recovered from the chloroform eluate and recrystallized from acetonitrile. By the above procedure was obtained 1.03 g of 7-ethyl-3-cyano-1-azaxanthone, m.p. 183°–185° C.

The following compounds were produced in the same manner as above.

| Starting compound | Product | m.p. (°C.)/ Recrys. solvent |
|---|---|---|
| 2-Amino-6-methyl-4-oxo-4H-1-benzopyran-3-carboxaldehyde | 7-Methyl-3-cyano-1-azaxanthone | 240–242° Ethanol |
| 2-Amino-4-oxo-4H-1-benzopyran-3-carboxaldehyde | 3-Cyano-1-azaxanthone | 220–226 Ethanol |
| 2-Amino-6-isopropyl-4-oxo-4H-1-benzopyran-3-carboxaldehyde | 7-Isopropyl-3-cyano-1-azaxanthone | 203–205 Ethanol |
| 2-Amino-6-chloro-4-oxo-4H-1-benzopyran-3-carboxaldehyde | 7-Chloro-3-cyano-1-azaxanthone | 286–288 Dimethylformamide |
| 2-Amino-6,8-dimethyl-4-oxo-4H-1-benzopyran-3-carboxaldehyde | 7,9-Dimethyl-3-cyano-1-azaxanthone | 254–257 Acetonitrile |
| 2-Amino-6-tert.-butyl-4-oxo-4H-1-benzopyran-3-carboxaldehyde | 7-tert.-Butyl-3-cyano-1-azaxanthone | 247–249 Acetonitrile |

-continued

| Starting compound | Product | m.p. (°C.)/ Recrys. solvent |
|---|---|---|
| 3-carboxaldehyde | | |

REFERENCE EXAMPLE 19

In 20 ml of chloroform was dissolved 1.0 g of ethyl 7-ethyl-2-hydroxy-1-azaxanthone-3-carboxylate, and to the solution was added dropwise an excess amount of diazomethane dissolved in ether over a period of 15 minutes under stirring at room temperature.

The reaction mixture was further stirred for 45 minutes at room temperature and, then, to the mixture was added small amount of acetic acid to decompose the excess amount of diazomethane. The solvent was distilled off and, then, the residue was chromatographed on a column packed with 100 g of silica gel, and eluted with chloroformacetone-formic acid (20:1:0.1). The first fraction was recrystallized from acetone to obtain 615 mg of ethyl 7-ethyl-2-methoxy-1-azaxanthone-3-carboxylate as colorless needless, melting point. 145°–146° C.

Elemental analysis, for C$_{18}$H$_{17}$NO$_5$: Calcd.: C, 66.05; H, 5.42; N, 4.28. Found: C, 66.12; H, 5.23; N, 4.21.

Infrared absorption spectrum (Nujol) cm$^{-1}$: 1730, 1670, 1605, 1590, 1310, 1240, 1220, 815, 790

Nuclear magnetic resonance (CDCl$_3$) δ: 9.17(1H, s), 8.13(1H, b.s.), 7.55(2H, m), 4.43(2H, q, J=7 Hz), 4.20(3H, s), 2.82(2H, q, J=7 Hz), 1.43(3H, t, J=7 Hz), 1.32(3H, t, J=7 Hz)

REFERENCE EXAMPLE 20

To a mixture of 25 ml of phosphoryl trichloride and 3 g of phosphorus pentachloride was added 974 mg of ethyl 7-ethyl-2-hydroxy-1-azaxanthone-3-carboxylate under stirring at 120° C. for 12 hours and then, phosphoryl trichloride was distilled off under reduced pressure. To the residue, ethanol was added gradually under ice-cooling to dissolve the residue. The solvent was then distilled off and the residue was chromatographed on silica gel. The desired product was eluted with benzene and recrystallized from isopropylether, whereby was obtained 658 mg of ethyl 7-ethyl-2-chloro-1-azaxanthone-3-carboxylate as colorless crystals, melting point: 160°–161° C.

Elemental analysis, for C$_{17}$H$_{14}$NO$_4$Cl: Calcd.: C, 61.54; H, 4.25; N, 4.22. Found: C, 61.46; H, 3.98; N, 4.27.

Infrared absorption spectrum (Nujol) cm$^{-1}$: 1720, 1658, 1585, 1265, 1210, 1130

Nuclear magnetic resonance (CDCl$_3$) δ: 1.30(3H, t, J=7 Hz), 1.43(3H, t, J=7 Hz), 2.73(2H, q, J=7 Hz), 4.46(2H, q, J=7 Hz), 7.43(1H, d, J=8 Hz), 7.63(1H, dd, J=2 & 8 Hz), 8.03(1H, d, J=2 Hz), 9.06(1H, s)

REFERENCE EXAMPLE 21

In 20 ml of chloroform was dissolved 884 mg of ethyl 7-ethyl-2-chloro-1-azaxanthone-3-carboxylate and to the resultant solution was added 3 ml of 30% methylamine-ethanol solution. The mixture was stirred at room temperature for 2 hours and then the solvent was distilled off. Water was added to the residue and the resultant precipitate was collected by filtration and recrystallized from dimethylformamide. By the above procedure was obtained 730 mg of ethyl 7-ethyl-2-methylamino-1- azaxanthone-3-carboxylate as colorless crystals, melting at 205°–207° C.

Elemental analysis, for $C_{18}H_{18}N_2O_4$: Calcd.: C, 66.24; H, 5.56; N, 8.58. Found: C, 66.22; H, 5.47; N, 8.74.

Infrared absorption spectrum (Nujol) cm$^{-1}$: 3250, 1660, 1610, 1582, 1280, 1240

Nuclear magnetic resonance ($CF_3COOD$) δ: 1.36(3H, t, J=7 Hz), 1.53(3H, t, J=7 Hz), 2.90(2H, q, J=7 Hz), 3.50(3H, s), 4.60(2H, q, J=7 Hz), 7.60(1H, d, J=8 Hz), 7.90(1H, dd, J=2 & 8 Hz), 8.20(1H, d, J=2 Hz), 9.43(1H, s)

REFERENCE EXAMPLE 22

A mixture consisting of 2.17 g of 2-amino-6-ethyl-4-oxo-4H-1-benzopyran-3-carboxaldehyde, 25 ml of dimethylformamide, 5 g of ethyl propiolate and 0.1 ml of triethylamine was stirred at 90° C. for one hour and then the mixture was allowed to stand at room temperature. The resulting crystals were collected by filtration and recrystallized from acetone to obtain 1.65 g of ethyl 3-(6-ethyl-3-formyl-4-oxo-4H-1-benzopyran-2-yl)aminoacrylate as colorless needles melting at 201°–203° C.

Infrared absorption spectrum (KBr) cm$^{-1}$: 3070, 1700, 1665, 1635

Nuclear magnetic resonance spectrum ($CDCl_3$) δ: 13.50(1H, d, J=12 Hz), 10.36(1H, s), 8.02(1H, d, J=2 Hz), 7.17–7.73(3H, m), 5.42(1H, d, J=9 Hz), 4.34(2H, q, J=7 Hz), 2.75(2H, q, J=7 Hz), 1.35(3H, t, J=7 Hz), 1.28(3H, t, J=7 Hz)

Elemental analysis, for $C_{17}H_{17}NO_5$: Calcd.: C, 64.75; H, 5.43; N, 4.44. Found: C, 64.72; H, 5.40; N, 4.33.

By a procedure similar to that described above, ethyl 3-(2-formyl-benzo[f]-chromon-2-yl)aminoacrylate was obtained from 2-aminobenzo[f]chromone-3-carboxaldehyde, m.p. 228°–230° C. (decomp.) (recrys.solvent: chloroform-petroleum benzine).

REFERENCE EXAMPLE 23

A mixture consisting of 1.58 g of ethyl 3-(6-ethyl-3-formyl-4-oxo-4H-1-benzopyran-2-yl)aminoacrylate obtained in Reference Example 22, 15 ml of dimethylformamide and 5 ml of triethylamine was refluxed at 130° C. for 2.5 hours. The reaction mixture was concentrated and to the residue was added about 50 ml of ethanol. The ethanol solution was cooled and the precipitated crystals were collected by filtration and recrystallized from ethanol to obtain 920 mg of ethyl 7-ethyl-1-azaxanthone-3-carboxylate as light-yellow needles, m.p. 140°–142° C.

Infrared absorption spectrum (KBr) cm$^{-1}$: 1725, 1670

Nuclear magnetic resonance spectrum ($CDCl_3$) δ: 9.27(2H, m), 8.11(1H, near s), 7.42–7.82(2H, m), 4.51(2H, q, J=7 Hz), 2.83(2H, q, J=8 Hz), 1.48 & 1.38(3H×2, t & t)

Elemental analysis, for $C_{17}H_{15}NO_4$: Calcd.: C, 68.67; H, 5.08; N, 4.71. Found: C, 68.86; H, 4.80; N, 4.85.

By a procedure similar to that described above, ethyl benzo[h]-1-azaxanthone-3-carboxylate melting at 186°–188° C. (recrys. solvent: acetone) was obtained from ethyl 3-(3-formyl-benzo[f]chromon-2-yl)aminoacrylate.

REFERENCE EXAMPLE 24

To 70 ml of dimethylformamide was added 2.2 g of 2-amino-4-oxo-4H-1-benzopyran-3-carboxaldehyde, followed by the addition of 2.5 g of cyanoacetylene. The mixture was heated under stirring at 140° C. for 15 hours and the solvent was then distilled off under reduced pressure. The residue was chromatographed on silica gel and eluted with chloroform and recrystallized from acetonitrile to give 0.83 g of 3-cyano-1-azaxanthone as crystals, m.p. 220°–226° C.

Nuclear magnetic resonance spectrum (DMSO-$d_6$) δ: 7.4–8.4(4H, m), 9.10(1H, d, J=2 Hz), 9.30(1H, d, J=2 Hz).

Elemental analysis, for $C_{13}H_6N_2O_2$: Calcd.: C, 70.27; H, 2.72; N, 12.61. Found: C, 70.12; H, 2.55; N, 12.50.

The following compounds were produced by procedures similar to the above.

| Starting compound | Product | m.p. (°C.)/ Recrys. solvent |
|---|---|---|
| 2-Amino-6-methyl-4-oxo-4H-1-benzopyran-3-carboxaldehyde | 7-Methyl-3-cyano-1-azaxanthone | 240–242 Ethyl acetate |
| 2-Amino-6-ethyl-4-oxo-4H-1-benzopyran-3-carboxaldehyde | 7-Ethyl-3-cyano-1-azaxanthone | 183–185 Acetonitrile |
| 2-Amino-6-isopropyl-4-oxo-4H-1-benzopyran-3-carboxaldehyde | 7-Isopropyl-3-cyano-1-azaxanthone | 203–205 Ethanol |
| 2-Amino-6,8-dimethyl-4-oxo-4H-1-benzopyran-3-carboxaldehyde | 7,9-dimethyl-3-cyano-1-azaxanthone | 254–257 Acetonitrile |

REFERENCE EXAMPLE 25

To a solution of 0.5 g of 7-isopropyl-2-amino-3-cyano-1-azaxanthone in 80 ml of acetic acid was added gradually 1.0 g of sodium nitrite at 70° C. After one hour period, 3 ml of water was added to the mixture which was heated at 70° C. for a further one hour. The solvent was distilled off under reduced pressure and then, to the residue, water was added. The yellow precipitate was collected by filtration, rinsed with water and recrystallized from ethanol to give 7-isopropyl-2-hydroxy-3-cyano-1-azaxanthone as yellow crystals, m.p.>300° C.

Elemental analysis, for $C_{16}H_{12}N_2O_3$: Calcd.: C, 68.56; H, 4.32; N, 10.00. Found: C, 68.28; H, 4.34; N, 9.70.

EXAMPLE 1

To 5 ml of 55% sulfuric acid was added 933 mg of ethyl 7-ethyl-2-methyl-1-azaxanthone-3-carboxylate and the mixture was stirred at 130° C. for one hour. After cooling, 100 ml of ice-water was added to the reaction mixture and the precipitate was recovered by filtration and crystallized from ethyl acetate and acetone in the order mentioned. By the above procedure was obtained 510 mg crystals of 7-ethyl-2-methyl-1-azaxanthone-3-carboxylic acid melting at 243°–245° C.

Elemental analysis, for $C_{16}H_{13}NO_3$: Calcd.: C, 67.84; H, 4.63; N, 4.95. Found: C, 67.75; H, 4.43; N, 4.89.

The following compounds were produced by procedures similar to that described above.

| Starting compound | Product | m.p. (°C.)/ Recrys. solvent |
|---|---|---|
| Ethyl 2-methyl-1-azaxanthone-3-carboxylate | 2-Methyl-1-azaxanthone-3-carboxylic acid | >300 80% Dimethylformamide |
| Ethyl 7-methoxy-2-methyl-1-azaxanthone- | 7-Methoxy-2-methyl-1-azaxanthone-3- | 294–295 Dimethyl- |

-continued

| Starting compound | Product | m.p. (°C.)/ Recrys. solvent |
|---|---|---|
| 3-carboxylate | carboxylic acid | formamide |
| Ethyl 2,7,9-trimethyl-1-azaxanthone-3-carboxylate | 2,7,9-trimethyl-1-azaxanthone-3-carboxylic acid | >300 Acetic acid |
| Ethyl 7-chloro-2-methyl-1-azaxanthone-3-carboxylate | 7-Chloro-2-methyl-1-azaxanthone-3-carboxylic acid | 292-294 Ethanol |
| Ethyl 7-nitro-2-methyl-1-azaxanthone-3-carboxylate | 7-Nitro-2-methyl-1-azaxanthone-3-carboxylic acid | >300 Dimethylformamide |
| Methyl 2-n-propyl-1-azaxanthone-3-carboxylate | 2-n-Propyl-1-azaxanthone-3-carboxylic acid | 217-218 Ethanol |
| Ethyl 7-ethyl-2-phenyl-1-azaxanthone-3-carboxylate | 7-Ethyl-2-phenyl-1-azaxanthone-3-carboxylic acid | 268-269 Ethyl acetate |

EXAMPLE 2

A mixture of 1.56 g of ethyl 2-amino-7-ethyl-1-azaxanthone-3-carboxylate, 10 ml of acetic acid and 10 ml of 55% sulfuric acid was stirred at 130° C. for 4 hours and, after water was added, the precipitate was collected by filtration and recrystallized from acetic acid-water. By the above procedure was obtained 1.28 g colorless needles of 2-amino-7-ethyl-1-azaxanthone-3-carboxylic acid, m.p. 313°-314° C. (decomp.).

Elemental analysis, for $C_{15}H_{12}N_2O_4$: Calcd.: C, 63.38; H, 4.26; N, 9.86. Found: C, 63.24; H, 4.56; N, 9.70.

The following compounds were produced by procedures similar to that described above.

| Starting compound | Product | m.p. (°C.)/ Recrys. solvent |
|---|---|---|
| Ethyl 2-amino-1-azaxanthone-3-carboxylate | 2-Amino-1-azaxanthone-3-carboxylic acid | >330 Dimethylformamide-water |
| Ethyl 2-amino-7-methoxy-1-azaxanthone-3-carboxylate | 2-Amino-7-methoxy-1-azaxanthone-3-carboxylic acid | 337-339 (decomp.) Dimethylformamide |
| Ethyl 2-amino-7,9-dimethyl-1-azaxanthone-3-carboxylate | 2-Amino-7,9-dimethyl-1-azaxanthone-3-carboxylic acid | >330 Dimethylformamide-water |
| Ethyl 2-amino-7-chloro-1-azaxanthone-3-carboxylate | 2-Amino-7-chloro-1-azaxanthone-3-carboxylic acid | 320-322 (decomp.) Dimethylformamide |
| Ethyl 2-amino-7-methyl-1-azaxanthone-3-carboxylate | 2-Amino-7-methyl-1-azaxanthone-3-carboxylic acid | >300 Dimethylformamide |
| Ethyl 2-amino-7-isopropyl-1-azaxanthone-3-carboxylate | 2-Amino-7-isopropyl-1-azaxanthone-3-carboxylic acid | >300 Dimethylformamide |
| Ethyl 2-amino-9-methoxy-1-azaxanthone-3-carboxylate | 2-Amino-9-methoxy-1-azaxanthone-3-carboxylic acid | >300 Dimethylformamide |
| Ethyl 2-amino-7-n-butyl-1-azaxanthone-3-carboxylate | 2-Amino-7-n-butyl-1-azaxanthone-3-carboxylic acid | 303-304 Dimethylformamide |
| Ethyl 2-amino-benzo-(h)-1-azaxanthone-3-carboxylate | 2-Amino-benzo(h)-1-azaxanthone-3-carboxylic acid | >300 Dimethylformamide |
| Ethyl 2-amino-8-hydroxy-1-azaxanthone-3-carboxylate | 2-Amino-8-hydroxy-1-azaxanthone-3-carboxylic acid | >300 Dimethylformamide |

EXAMPLE 3

A mixture of 1.0 g of ethyl 1-azaxanthone-3-carboxylate, 8 ml of glacial acetic acid and 8 ml of 55% sulfuric acid was stirred under reflux at 130° C. for 4 hours. After cooling, the precipitate was recovered by filtration, rinsed with water and recrystallized from 70% dimethylformamide. By the above procedure was obtained 822 mg of 1-azaxanthone-3-carboxylic acid as colorless needles, m.p. 272° C.

Infrared absorption spectrum (KBr) cm$^{-1}$: 1700, 1670, 1615, 1605

Nuclear magnetic resonance spectrum (DMSO-d$_6$) δ: 9.28(1H, d, J=2 Hz), 8.97(1H, d, J=2 Hz), 8.17(1H, dd, J=2 & 8 Hz), 7.3-8.0(3H, m)

Elemental analysis, for $C_{13}H_7NO_4$: Calcd.: C, 64.73; H, 2.93; N, 5.81. Found: C, 64.51; H, 2.77; N, 5.63.

The following compounds were produced by procedures similar to that described above.

| Starting compound | Product | m.p. (°C.)/ Recrys. Solvent |
|---|---|---|
| Ethyl 7-chloro-1-azaxanthone-3-carboxylate | 7-Chloro-1-azaxanthone-3-carboxylic acid | 300-301 70% Dimethylformamide |
| Ethyl 7-nitro-1-azaxanthone-3-carboxylate | 7-Nitro-1-azaxanthone-3-carboxylic acid | >300, 70% Dimethylformamide |
| Ethyl 7-ethyl-1-azaxanthone-3-carboxylate | 7-Ethyl-1-azaxanthone-3-carboxylic acid | 238-239 Acetone |
| Ethyl benzo(h)-1-azaxanthone-3-carboxylate | Benzo(h)-1-azaxanthone-3-carboxylic acid | >300 Dimethylformamide |

EXAMPLE 4

A mixture consisting of 341 mg of dimethyl 7-ethyl-1-azaxanthone-2,3-dicarboxylate, 2 ml of acetic acid and 2 ml of 55% sulfuric acid was stirred at 130° C. for 4 hours. After cooling, water was added and the precipitate was collected by filtration and heated carefully in a round bottomed flask over a direct fire, whereupon it was fused with foaming. After the foaming had subsided, the fused mass was cooled and recrystallized from acetone. By the above procedure was obtained 124 mg of 7-ethyl-1-azaxanthone-3-carboxylic acid as colorless needles, m.p. 238°-239° C.

Infrared absorption spectrum (Nujol) cm$^{-1}$: 1690, 1675

Nuclear magnetic resonance spectrum (DMSO-d$_6$) δ: 9.08(1H, d, J=2 Hz), 8.81(1H, d, J=2 Hz), 7.80(1H, s), 7.69(H, dd, J=2 & 8 Hz), 7.49(1H, d, J=8 Hz), 2.75 (2H, q, J=7 Hz), 1.24(3H, t, J=7 Hz)

Elemental analysis, for $C_{15}H_{11}NO_4$: Calcd.: C, 66.91; H, 4.12; N, 5.20. Found: C, 66.71; H, 3.94; N, 5.10.

EXAMPLE 5

A mixture consisting of 1.5 g of dimethyl 7-chloro-1-azaxanthone-2,3-dicarboxylate, 10 ml of 55% sulfuric acid and 10 ml of glacial acetic acid was stirred at 130° C. for 6 hours. After cooling, the precipitate was collected by filtration, rinsed with water and crystallized from 70% dimethylformamide. By the above procedure was obtained 723 mg of 7-chloro-1-azaxanthone-2,3-dicarboxylic acid as colorless needles, m.p. 266°-269° C. (decomp.). Nuclear magnetic resonance spectrum (DMSO-d$_6$) δ: 7.9–8.1(2H, m), 8.20(1H, d, J=2 Hz), 9.03(1H, s)

EXAMPLE 6

A mixture consisting of 170 mg of diethyl 7-ethyl-1l-azaxanthone-2,3-dicarboxylate, 1 ml of acetic acid and 1 ml of 55% sulfuric acid was heated at 130° C. for 3 hours and the precipitate was collected by filtration and recrystallized from acetic acid. By this procedure was obtained 30 mg of 7-ethyl-1-azaxanthone-2,3-dicarboxylic acid as crystals melting at 210°–211° C. (decomp.).

Infrared absorption spectrum (Nujol) cm$^{-1}$: 1728, 1695, 1675

Nuclear magnetic resonance spectrum (DMSO-d$_6$) δ: 8.93(1H, s), 7.97(1 H, d, J=2 Hz), 7.80(1H, dd, J=2 & 9 Hz), 7.62(1H, d, J=9 Hz), 2.78(2H, q, J=7 Hz), 1.27 (3H, t, J=7 Hz).

EXAMPLE 7

A mixture consisting of 185 mg of diethyl 7, 9-dimethyl-1-azaxanthone-2,3-dicarboxylate, 1 ml of acetic acid and 1 ml of 55% sulfuric acid was heated at 130° C. for 2 hours and the sparingly soluble product was recovered by filtration. It was dissolved in a saturated aqueous solution of sodium hydrogen carbonate and the small amount of sparingly soluble product was filtered off. The filtrate was made acidic and the precipitate was collected by filtration and recrystallized from acetic acid-water. By the above procedure was obtained 20 mg of 7,9-dimethyl-1-azaxanthone-2,3-dicarboxylic acid as pale yellow needles, m.p. 175°–177° C. (depolarization point)

Infrared absorption spectrum (Nujol) cm$^{-1}$: 1725–1710, 1670

Nuclear magnetic resonance spectrum (DMSO-d$_6$) δ: 9.17(1H, s), 7.85(1H, d, J=2 Hz), 7.65(1H, d, J=2 Hz), 2.53(3H, s), 2.45(3H, s)

EXAMPLE 8

A mixture consisting of 700 mg of ethyl 7-ethyl-2-hydroxy-1-azaxanthone-3-carboxylate, 20 ml of glacial acetic acid and 10 ml of 55% sulfuric acid was stirred under reflux at 130° C. for 5 hours. After cooling, the precipitate was collected by filtration, rinsed with water and recrystallized from dimethylformamide. By the above procedure was obtained 492 mg of 7-ethyl-2-hydroxy-1-axaxanthone-3-carboxylic acid as colorless platelets melting at 292°–296° C.

Infrared absorption spectrum (KBr) cm$^{-1}$: 1740, 1675, 1610

Nuclear magnetic resonance spectrum (DMSO-d$_6$) δ: 1.25(3H, t, J=7 Hz), 2.75(2H, q, J=7 Hz), 7.45(1H, d, J=9 Hz), 7.70(1H, dd, J=9 & 2 Hz), 7.83(1H, d, J=2 Hz), 8.74(1H, s)

EXAMPLE 9

A mixture consisting of 600 mg of ethyl 2-hydroxy-1-azaxanthone-3-carboxylate, 10 ml of glacial acetic acid and 5 ml of 55% sulfuric acid was stirred under reflux at 130° C. for 4 hours. After cooling, the precipitate was collected by filtration, rinsed with water and recrystallized from dimethylformamide. By the above procedure was obtained 418 mg of 2-hydroxy-1-azaxanthone-3-carboxylic acid as white crystals, m.p. higher than 300° C.

Infrared absorption spectrum (KBr) cm$^{-1}$: 1745, 1660, 1620

Nuclear magnetic resonance spectrum (DMSO-d$_6$) δ: 7.6–8.1(3H, m), 8.17(1H, dd, J=8 & 2 Hz), 8.82(1H, s).

The following compounds were produced in the same manner as above.

| Starting compound | Product | m.p. (°C.)/ Recrys. solvent |
|---|---|---|
| Ethyl 7-methyl-2-hydroxy-1-azaxanthone-3-carboxylate | 7-Methyl-2-hydroxy-1-azaxanthone-3-carboxylic acid | >300 Dimethylformamide |
| Ethyl 7-methoxy-2-hydroxy-1-azaxanthone-3-carboxylate | 7-Methoxy-2-hydroxy-1-azaxanthone-3-carboxylic acid | >300 Dimethylformamide |
| Ethyl 9-methoxy-2-hydroxy-1-azaxanthone-3-carboxylate | 9-Methoxy-2-hydroxy-1-azaxanthone-3-carboxylic acid | >300 Dimethylformamide |
| Ethyl 2-hydroxy-7,9-dimethyl-1-azaxanthone-3-carboxylate | 2-Hydroxy-7,9-dimethyl-1-azaxanthone-3-carboxylic acid | >300 Dimethylformamide |
| Ethyl 7-n-butyl-2-hydroxy-1-azaxanthone-3-carboxylate | 7-n-butyl-2-hydroxy-1-azaxanthone-3-carboxylic acid | 304–305 Dimethylformamide-Ethanol |

EXAMPLE 10

A mixture of 500 mg of ethyl 7-ethyl-2-methoxy-1-azaxanthone-3-carboxylate, 10 ml of acetic acid and 5 ml of 55% sulfuric acid was stirred at 80° C. for 2 hours, followed by the addition of 20 ml of water and further stirred at that temperature for 10 minutes. After cooling, the resultant precipitate was collected by filtration, rinsed with water, dried and dissolved in 3 ml of dimethylformamide. To the resultant solution was added 3 g of silica gel and stirred well, and then the dimethylformamide was distilled off. The residue was layered on a column of 50 g of silica gel and eluted with a solution of chloroform-acetone-formic acid (9:1:0.1) to obtain about 390 mg of crystals, which was recrystallized from dimethylformamide-ethanol to obtain 358 mg of 7-ethyl-2-methoxy-1-azaxanthone-3-carboxylic acid as colorless needles, m.p. 226°–228° C.

Elemental analysis, for $C_{16}H_{13}NO_5$: Calcd.: C, 64.21; H, 4.38; N, 4.68. Found: C, 64.10; H, 4.24; N, 4.71.

Infrared absorption spectrum (Nujol) cm$^{-1}$: 1690, 1660, 1600, 1590, 1290, 825, 790

Nuclear magnetic resonance spectrum (DMSO-d$_6$) δ: 8.70(1H, s), 7.80(1H, m), 7.40–7.63(2H, m), 4.05 (3H, s), 2.73(2H, q, J=7.5 Hz), 1.23(3H, t, J=7.5 Hz)

EXAMPLE 11

In 3.5 ml of 50% sulfuric acid-acetic acid (1:1) was dissolved 681 mg of ethyl 7-ethyl-2-methylamino-1-azaxanthone-3-carboxylate. The solution was heated at 100° C. for 6 hours and then adjusted to pH 5 with 10% sodium hydroxide. The resultant precipitate was collected by filtration, rinsed with water and recrystallized from dimethylformamide-ethanol to obtain 488 mg of 7-ethyl-2-methylamino-1-azaxanthone-3-carboxylic acid as crystals, m.p.>300° C.

Elemental analysis, for $C_{16}H_{14}N_2O_4$: Calcd.: C, 64.42; H, 4.73; N, 9.39. Found: C, 64.24; H, 4.50; N, 9.19.

Infrared absorption spectrum (Nujol) cm$^{-1}$: 3270, 1690, 1605, 1570, 1300, 1127

Nuclear magnetic resonance spectrum (DMSO-d$_6$) δ: 1.25(3H, t, J=7.5 Hz), 2.73(2H, q, J=7.5 Hz), 3.03(3H, d, J=4 Hz), 7.2–7.8(2H, m), 7.80(1H, d, J=2 Hz), 8.70(1H, s)

EXAMPLE 12

In a mixture of 10 ml of 50% aqueous sulfuric acid and 10 ml of acetic acid, 0.875 g of 7-isopropyl-3-cyano-1-azaxanthone was stirred at 120° C. for 2 hours. After completion of the reaction, water was added to the reaction mixture and the resultant precipitate was collected by filtration, rinsed with water, dried and recrystallized from ethanol. By the above procedure was obtained 0.623 g of 7-isopropyl-1-azaxanthone-3-carboxylic acid, m.p. 259°–261° C.

The following compounds were produced in the same manner.

| Starting compound | Product | m.p. (°C.)/ Recrys. solvent |
| --- | --- | --- |
| 1-Azaxanthone-3-carbonitrile | 1-Azaxanthone-3-carboxylic acid | 267–269 Ethyl acetate |
| 7-Ethyl-1-azaxanthone-3-carbonitrile | 7-Ethyl-1-azaxanthone-3-carboxylic acid | 238–239 Dimethylformamide |
| 2-Amino-7-dimethylamino-1-azaxanthone-3-carbonitrile | 2-Amino-7-dimethylamino-1-azaxanthone-3-carboxylic acid . 2H$_2$SO$_4$ | 258–260 (Decomp.) Acetic acid |
| 7-tert.-Butyl-1-azaxanthone-3-carbonitrile | 7-tert.-Butyl-1-azaxanthone-3-carboxylic acid | 225–228 Ethanol |

EXAMPLE 13

A mixture of 27 mg of 7-ethyl-1-azaxanthone-3-carboxylic acid, 12 mg of diethanolamine and 10 ml of ethanol was dissolved under heating. The solution was concentrated and, after cooling, the precipitated crystals were collected by filtration. By the above procedure was obtained 25 mg of 7-ethyl-1-azaxanthone-3-carboxylic acid diethanolamine salt as colorless crystals melting at 162°–164° C.

Elemental analysis, for C$_{19}$H$_{22}$N$_2$O$_6$: Calcd. C, 60.95; H, 5.92; N, 7.48. Found: C, 60.70; H, 5.87; N, 7.49.

What we claim is:

1. A compound of the formula

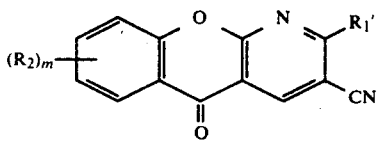

wherein:

m is 1 or 2;

R$'_1$ is hydrogen, C$_{1-6}$ alkyl, phenyl C$_{1-6}$ alkoxy-carbonyl, hydroxy, C$_{1-4}$ alkoxy, amino or C$_{1-3}$ alkylamino; and each R$_2$ is independently C$_{1-6}$ alkyl, C$_{1-4}$ alkoxy, halogen, nitro, hydroxy, carboxy, amino, C$_{1-3}$ alkylamino or di(C$_{1-3}$ alkyl) amino.

2. A compound of claim 1, wherein R$_2$ is C$_{1-4}$ alkoxy, halogen, nitro, hydroxy, carboxy, amino, C$_{1-3}$ alkylamino or di(C$_{1-3}$alkyl)amino.

3. A compound as claimed in claim 1, wherein m is 1.

4. A compound as claimed in claim 1, wherein m is 2.

5. A compound as claimed in claim 1, wherein R$'_1$ is hydrogen.

6. A compound as claimed in claim 1, wherein R$'_1$ is amino.

7. A compound as claimed in claim 1, wherein R$'_1$ is hydroxy.

8. A compound as claimed in claim 1, wherein R$_2$ is C$_{1-6}$ alkyl.

9. A compound as claimed in claim 1, wherein R$_2$ is C$_{1-4}$ alkoxy.

10. A compound as claimed in claim 1, wherein R$_2$ is di(C$_{1-3}$ alkyl) amino.

11. A compound as claimed in claim 1, wherein R$_2$ is halogen.

12. A compound as claimed in claim 1, wherein the compound is 2-amino-7-ethyl-3-cyano-1-azaxanthone.

13. A compound as claimed in claim 1, wherein the compound is 2-amino-7-chloro-3-cyano-1-azaxanthone.

14. A compound as claimed in claim 1, wherein the compound is 2-amino-7-dimethylamino-3-cyano-1-azaxanthone.

15. A compound as claimed in claim 1, wherein the compound is 2-amino-7-isopropyl-3-cyano-1-azaxanthone.

16. A compound as claimed in claim 1, wherein the compound is 2-amino-7-methyl-3-cyano-1-azaxanthone.

17. A compound as claimed in claim 1, wherein the compound is 7-methyl-3-cyano-1-azaxanthone.

18. A compound as claimed in claim 1, wherein the compound is 7-ethyl-3-cyano-1-azaxanthone.

19. A compound as claimed in claim 1, wherein the compound is 7-isopropyl-3-cyano-1-azaxanthone.

20. A compound as claimed in claim 1, wherein the compound is 7,9-dimethyl-3-cyano-1-azaxanthone.

21. A compound as claimed in claim 1, wherein the compound is 7-isopropyl-2-hydroxy-3-cyano-1-azaxanthone.

22. A compound as claimed in claim 1, wherein the compound is 7-tert.-butyl-3-cyano-1-azaxanthone.

23. A compound as claimed in claim 1, wherein the compound is 7-chloro-3-cyano-1-azaxanthone.

* * * * *